United States Patent
Radhakrishnan et al.

(10) Patent No.: US 8,753,679 B2
(45) Date of Patent: Jun. 17, 2014

(54) CAPSULE FORMULATION OF PIRFENIDONE AND PHARMACEUTICALLY ACCEPTABLE EXCIPIENTS

(71) Applicant: Intermune, Inc., Brisbane, CA (US)

(72) Inventors: Ramachandran Radhakrishnan, Fremont, CA (US); Ronald Vladyka, Somerset, NJ (US); Kenneth Sultzbaugh, Bridge Water, NJ (US)

(73) Assignee: Intermune, Inc., Brisbane, CA (US)

( * ) Notice: Subject to any disclaimer, the term of this patent is extended or adjusted under 35 U.S.C. 154(b) by 0 days.

(21) Appl. No.: 13/776,079

(22) Filed: Feb. 25, 2013

(65) Prior Publication Data

US 2013/0165484 A1     Jun. 27, 2013

Related U.S. Application Data

(63) Continuation of application No. 13/162,048, filed on Jun. 16, 2011, now Pat. No. 8,383,150, which is a continuation of application No. 12/067,712, filed as application No. PCT/US2006/037057 on Sep. 22, 2006, now Pat. No. 7,988,994.

(60) Provisional application No. 60/720,257, filed on Sep. 22, 2005.

(51) Int. Cl.
*A61K 9/48* (2006.01)
*A61K 31/44* (2006.01)

(52) U.S. Cl.
USPC .......................................... 424/452; 514/345

(58) Field of Classification Search
USPC .......................................... 424/452; 514/345
See application file for complete search history.

(56) References Cited

U.S. PATENT DOCUMENTS

| | | | |
|---|---|---|---|
| 3,974,281 A * | 8/1976 | Gadekar | ........................ 514/345 |
| 4,042,699 A | 8/1977 | Gadekar | |
| 4,052,509 A | 10/1977 | Gadekar | |
| 5,310,562 A | 5/1994 | Margolin | |
| 5,518,729 A | 5/1996 | Margolin | |
| 5,591,766 A | 1/1997 | Bang et al. | |
| 5,716,632 A | 2/1998 | Margolin | |
| 6,090,822 A | 7/2000 | Margolin | |

(Continued)

FOREIGN PATENT DOCUMENTS

| | | |
|---|---|---|
| EP | 0383591 | 8/1990 |
| EP | 0458861 A1 | 12/1991 |

(Continued)

OTHER PUBLICATIONS

"Phase II Trial of Pirfenidone in Children, Adolescents, and Young Adults with Neurofibromatosis Type I and Progressive Plexiform Neurofibromas," NIH Clinical Research Studies, Protocol Number: 04-C-0080 (Last Update: Feb. 28, 2009).

(Continued)

*Primary Examiner* — Aradhana Sasan
(74) *Attorney, Agent, or Firm* — Marshall, Gerstein & Borun LLP

(57) ABSTRACT

A capsule formulation of pirfenidone is provided that includes pharmaceutically acceptable excipients. In one embodiment, this capsule formulation is capable of sustaining desirable pharmacokinetic responses in a patient. Further provided are methods of treating fibrotic conditions and other cytokine-mediated disorders by administering pirfenidone capsules of such formulation to a patient in need.

26 Claims, 10 Drawing Sheets

Storage conditions: 40° C/75%RH

| Attributes | Time (months) | | | | | | | |
|---|---|---|---|---|---|---|---|---|
| | 0 | 1 | 2 | 3 | 6 | 9 | 12 | 18 |
| Appearance | Conforms | Conforms | Conforms | Conforms | Conforms | Conforms | Conforms | Conforms |
| Assay (%) | 99.6 | 101.0 | 100.3 | 100.7 | 101.3 | 101.6 | 100.4 | 101.0 |
| Dissolution % (RSD) | 100 (2.1) | 101 (1.5) | 100 (3.7) | 98 (4.8) | 100 (3.8) | 100 (1.8) | 98 (3.3) | 42 (7.5) |
| Impurities (HPLC) % | < 0.05[a] | < 0.05 | < 0.05 | < 0.05 | < 0.05 | < 0.05 | < 0.05 | < 0.05 |
| Moisture % | 0.96 | 0.94 | 1.2 | 1.3 | 1.3 | 1.4 | 1.8 | 2.3 |

[a]No peaks detected at a Limit of Detection of 0.025 μg/mL

(56) References Cited

U.S. PATENT DOCUMENTS

| | | | |
|---|---|---|---|
| 6,300,349 B1* | 10/2001 | Margolin | 514/345 |
| 7,767,225 B2* | 8/2010 | Radhakrishnan et al. | 424/452 |
| 7,867,516 B2 | 1/2011 | Kiyonaka et al. | |
| 7,988,994 B2* | 8/2011 | Radhakrishnan et al. | 424/452 |
| 8,383,150 B2* | 2/2013 | Radhakrishnan et al. | 424/452 |
| 2004/0048902 A1* | 3/2004 | Kiyonaka et al. | 514/345 |
| 2007/0054842 A1 | 3/2007 | Blatt et al. | |
| 2011/0104276 A1 | 5/2011 | Kiyonaka et al. | |
| 2012/0183615 A1 | 7/2012 | Kiyonaka et al. | |
| 2013/0115288 A1 | 5/2013 | Kiyonaka et al. | |

FOREIGN PATENT DOCUMENTS

| | | |
|---|---|---|
| EP | 1138329 A2 | 10/2001 |
| EP | 1356816 | 10/2003 |
| WO | WO-90/09176 A1 | 8/1990 |
| WO | WO-94/26249 | 11/1994 |
| WO | WO-97/10712 | 3/1997 |
| WO | WO-2004/019758 A2 | 3/2004 |
| WO | WO-2004/019863 A2 | 3/2004 |
| WO | WO 2004/019863 A2 * | 3/2004 |
| WO | WO-2004/103296 A2 | 12/2004 |
| WO | WO-2005/016241 A2 | 2/2005 |
| WO | WO-2005/040758 A2 | 5/2005 |
| WO | WO-2005/047256 A1 | 5/2005 |

OTHER PUBLICATIONS

Azuma et al., "Double-blind, Placebo-controlled Trial of Pirfenidone in Patients with Idiopathic Pulmonary Fibrosis," Am J. Respir. Crit. Care Med. 171: 1040-47 (2005).
Cain et al., Inhabition of tumor necrosis factor and subsequent endotoxin shock by pirfenidone. Int. J. Immunopharmacol. 20: 685-95 (1998).
Combined PCT Search Report and Written Opinion, PCT/US2006/037057 (Apr. 23, 2007).
Examination Report from corresponding New Zealand patent application No. 591443, dated Jun. 22, 2012.
Examination Report, European Application No. 06815221.4, Dec. 9, 2011.
Examination Report, European Application No. 06815221.4, Oct. 25, 2010.
Examination Report, European Application No. 06815221.4, Sep. 26, 2012.
Examination Report, Nicaraguan National Phase Application No. 2008-000086, Jan. 18, 2013 (English translation).
Examination Report, Nicaraguan National Phase Application No. 2008/0086, Mar. 15, 2012 (English translation).
Examination Report, Philippines Application No. 1-2008-500545, Sep. 21, 2011.
Final office action, Japanese Patent Application No. 2008-532431, May 2013.
Gahl et al., "Effect of Pirfenidone on the Pulmonary Fibrosis of Hermansky-Pudlak Syndrome," Molecular Genetics and Metabolism 76: 234-42 (2002).
Gennaro (ed.), Remington Farmacia, Tomo 2, Editorial Medica Panamericana, 19th ed. pp. 2485-2489 (1995).
Georgian Search Report for corresponding Georgian Patent Application No. 10558/01 (Jun. 15, 2009).
InterMune, Dissolution Profile Comparison Study Report for Pirfenidone Capsules (2008).
International Preliminary Report on Patentability, PCT/US2006/037057 (Mar. 26, 2008).
Martinet et al., Exaggerated spontaneous release of platelet-derived growth factor by alveolar macrophages from patients with idiopathic pulmonary fibrosis. N. Engl. J. Med. 317: 202-9 (1987).
Nagai et al., Open-label compassionate use one year-treatment with pirfenidone to patients with chronic pulmonary fibrosis, Intern. Med. 41: 1118-23 (2002).
Notari, Biopharmaceutics and Clinical Pharmacokinetics: An Introduction, Marcel Dekker, Inc., New York and Basel, pp. 134-159 (4th ed. 1986).
Office Action from corresponding Colombian patent application No. 08029322, completed Apr. 2012.
Office action, Canadian patent application No. 2,620,380, Apr. 18, 2011.
Office action, Canadian patent application No. 2,620,380, Sep. 20, 2010.
Office Action, Japanese Patent Application No. 2008-532431, Apr. 17, 2012.
Office action, Korean patent application No. 10-2008-7006806, Aug. 21, 2012.
Office action, Mexican Patent Application No. Mx/a/2008/003882, Nov. 2010.
Office action, Vietnamese patent application No. 1-2008-00880, Aug. 12, 2010.
PCT Search Report, PCT/US2006/037057, Apr. 23, 2004.
Reexamination Notice, Chinese Patent Application No. 2006 80034874.2, Apr. 23, 2013.
Report on Deliberation Results, http://www.pmda.go.jp/english/service/pdf/Pirespa-Pirfenidone.pdf, Sep. 16, 2008.
Schmidt et al., Bioavailability of pirfenidone capsules following oral administration (human volunteers) (60-244-73). Affiliated Medical Research, Inc. Princeton, New Jersey (1974).
Shionogi & Co., Ltd., Pirespa® Tablet 200 mg Pirfenidone Tablet, Package Insert (Version 1, Oct. 2008) and English-language translation thereof.
Singapore Written Opinion (issued by the Danish Patent Ofifce) from corresponding Singaporean Patent Application No. 200801941-6 (Apr. 24, 2009).
Striker et al., Mesangial cell turnover: effect of heparin and peptide growth factor. Lab Invest. 64: 446-56 (1991).
U.S. Office Action, U.S. Appl. No. 12/067,712 (Nov. 15, 2010).
U.S. Office Action, U.S. Appl. No. 12/426,182 (Apr. 8, 2010).
U.S. Office Action, U.S. Appl. No. 12/426,182 (Nov. 18, 2009).
U.S. Office Action, U.S. Appl. No. 12/426,182 (Sep. 16, 2009).
Van Barneveld et al., Natural course of bleomycin-induced pneumonitis . A follow-up study.Am. Rev. Respir Dis. 135: 48-51 (1987).
Zhang et al., Pirfenidone reduces firbonectin synthesis by cultured human retinal pigment epithelial cells. Aust. N Z J. Ophthalmol. 26: S74-6 (1998).

* cited by examiner

Composition Table Of Shionogi Tablets

| Compound | Function | Strength |
|---|---|---|
| | | 200 mg Tablet |
| Intragranular additions | | |
| Pirfenidone | API | 200.0 |
| Lactose | Filler | 56.0 |
| Carmellose Calcium | Disintegrator | 5.0 |
| Hydroxymethyl cellulose | Binder | 6.0 |
| Extragranular additions | | |
| Carmellose Calcium | Disintegrator | 15.0 |
| Magnesium Stearate | Lubricant | 3.0 |
| Core Tablet | Total | 285.0 |
| Hydroxylpropyl cellulose | Coating Base | |
| Triethylene citrate | Plasticizer | 7.6 |
| Titanium dioxide | Light Protectant | 0.8 |
| Coating Layer Total | | 3.0 |
| Total | | 296.4 |

FIG. 2

Comparison of PK Parameters Between Capsule of Pirfenidone Only and Capsules with Excipients

| PK Parameters | Capsule Group I | Capsule Group II | Capsule of Pirfenidone Only |
|---|---|---|---|
| $C_{max}$ (μg/mL) | 8.05 ± 2.53 | 7.68 ± 1.86 | 6.28 ± 2.49 |
| $T_{max}$ (hr) | 3.23 ± 1.42 | 2.73 ± 1.17 | 0.85 ± 0.32 |
| AUC (μg/mL·hr) | 62.4 ± 25.4 | 59.3 ± 22.8 | 20.8 ± 10.0 |
| $T_{1/2}$ (hr) | 3.00 ± 0.98 | 2.93 ± 0.94 | 2.20 ± 0.60 |

FIG. 5

FOMULATION USED IN HUMAN AND IN VITRO

| Component | Quality Standard | Function | mg/Capsule |
|---|---|---|---|
| | | | 267 mg capsule |
| Pirfenidone | In-house | Active ingredient | 267 |
| Croscarmellose, sodium | NF, Ph Eur, JP | Disintegrant | 26.5 |
| Microcrystalline cellulose | USP, Ph Eur, JP | Binder, Filler | 24.0 |
| Povidone | USP, Ph Eur, JP | Binder | 6.0 |
| Magnesium stearate | NF, Ph Eur, JP | Lubricant | 1.5 |
| Purified water | USP | Processing solvent | -- |
| Gelatin capsule | USP, Ph Eur | -- | -- |
| Total weight per capsule | | | 325.0 |

FIG. 6

REPRESENTATIVE 45 KG BATCH FORMULA-267 MG CAPSULE DOSAGE STRENGTH

| Component | % (w/w) | kg |
|---|---|---|
| Pirfenidone | 82.15 | 36.97 |
| Croscarmellose Sodium | 8.15 | 3.67 |
| Microcrystalline Cellulose (Avicell PH 102) | 7.39 | 3.32 |
| Povidone (Nominal K Value: 30) | 1.85 | 0.83 |
| Magnesium Stearate | 0.46 | 0.21 |
| Purified Water | -- | 20.40 |
| Total Weight (kg) | 100 | 45.00 |

FIG. 7

Storage conditions: 25° C/60%RH

| Attributes | Time (months) | | | | | | | |
|---|---|---|---|---|---|---|---|---|
| | 0 | 1 | 2 | 3 | 6 | 9 | 12 | 18 |
| Appearance | Conforms | Conforms | Conforms | Conforms | Conforms | Conforms | Conforms | Conforms |
| Assay (%) | 99.6 | 101.0 | 101.2 | 100.6 | 101.3 | 101.7 | 101.1 | 100.6 |
| Dissolution % (RSD) | 100 (2.1) | 101 (2.5) | 99 (2.8) | 101 (4.5) | 99 (4.6) | 101 (1.2) | 101 (1.6) | 101 (1.7) |
| Impurities (HPLC) % | <0.05[a] | <0.05 | <0.05 | <0.05 | <0.05 | <0.05 | <0.05 | <0.05 |
| Moisture % | 0.96 | 0.86 | 1.0 | 1.2 | 1.4 | 1.2 | 1.4 | 1.7 |

[a]No peaks detected at a Limit of Detection of 0.025μg/mL

FIG. 8A

Storage conditions: 30° C/65%RH

| Attributes | Time (months) | | | | | | | |
|---|---|---|---|---|---|---|---|---|
| | 0 | 1 | 2 | 3 | 6 | 9 | 12 | 18 |
| Appearance | Conforms | Conforms | Conforms | Conforms | Conforms | Conforms | Conforms | Conforms |
| Assay (%) | 99.6 | 101.3 | 100.6 | 100.4 | 101.3 | 101.6 | 101.3 | 101.1 |
| Dissolution % (RSD) | 100 (2.1) | 95 (4.2) | 99 (1.3) | 101 (3.8) | 100 (3.8) | 100 (2.1) | 101 (2.3) | 99 (4.1) |
| Impurities (HPLC) % | <0.05[a] | <0.05 | <0.05 | <0.05 | <0.05 | <0.05 | <0.05 | <0.05 |
| Moisture % | 0.96 | 0.91 | 1.1 | 1.3 | 1.5 | 1.3 | 1.6 | 1.9 |

[a]No peaks detected at a Limit of Detection of 0.025μg/mL

FIG. 8B

Storage conditions: 40° C/75%RH

| Attributes | Time (months) | | | | | | | |
|---|---|---|---|---|---|---|---|---|
| | 0 | 1 | 2 | 3 | 6 | 9 | 12 | 18 |
| Appearance | Conforms | Conforms | Conforms | Conforms | Conforms | Conforms | Conforms | Conforms |
| Assay (%) | 99.6 | 101.0 | 100.3 | 100.7 | 101.3 | 101.6 | 100.4 | 101.0 |
| Dissolution % (RSD) | 100 (2.1) | 101 (1.5) | 100 (3.7) | 98 (4.8) | 100 (3.8) | 100 (1.8) | 98 (3.3) | 42 (7.5) |
| Impurities (HPLC) % | < 0.05[a] | < 0.05 | < 0.05 | < 0.05 | < 0.05 | < 0.05 | < 0.05 | < 0.05 |
| Moisture % | 0.96 | 0.94 | 1.2 | 1.3 | 1.3 | 1.4 | 1.8 | 2.3 |

[a] No peaks detected at a Limit of Detection of 0.025 µg/mL

FIG. 8C

Representative Medicinal Product Components and Composition for 267 mg dose Capsule version II

| Component | Quality Standard | Function | mg/capsule | % (w/w) |
|---|---|---|---|---|
| Pirfenidone | In-house[a] | Active ingredient | 227.5 | 70.0 |
| Croscarmellose, sodium | NF, Ph Eur, JP | Disintegrant | 44.6 | 13.7 |
| Microcrystalline cellulose[b] | USP, Ph Eur, JP | Binder, Filler | 40.3 | 12.4 |
| Povidone | USP, Ph Eur, JP | Binder | 10.1 | 3.1 |
| Magnesium stearate | NF, Ph Eur, JP | Lubricant | 2.5 | 0.8 |
| Purified water[c] | USP | Processing solvent | -- | -- |
| Gelatin capsule[d] | USP, Ph Eur | -- | -- | -- |
| Total weight per capsule | | | 325.0 | 100 |

FIG. 9A

Representative Medicinal Product Components and Composition for 267 mg dose Capsule version III

| Component | Quality Standard | Function | mg/capsule | % (w/w) |
|---|---|---|---|---|
| Pirfenidone | In-house[a] | Active ingredient | 308.8 | 95.0 |
| Croscarmellose, sodium | NF, Ph Eur, JP | Disintegrant | 7.4 | 2.3 |
| Microcrystalline cellulose[b] | USP, Ph Eur, JP | Binder, Filler | 6.7 | 2.1 |
| Povidone | USP, Ph Eur, JP | Binder | 1.7 | 0.5 |
| Magnesium stearate | NF, Ph Eur, JP | Lubricant | 0.4 | 0.1 |
| Purified water[c] | USP | Processing solvent | -- | -- |
| Gelatin capsule[d] | USP, Ph Eur | -- | -- | -- |
| Total weight per capsule | | | 325.0 | 100 |

FIG. 9B

CAPSULE FORMULATION OF PIRFENIDONE AND PHARMACEUTICALLY ACCEPTABLE EXCIPIENTS

CROSS REFERENCE TO RELATED APPLICATIONS

This is a continuation of U.S. patent application Ser. No. 13/162,048 filed Jun. 16, 2011 (U.S. Pat. No. 8,383,150), which is a continuation of U.S. patent application Ser. No. 12/067,712, filed Jul. 14, 2008 (U.S. Pat. No. 7,988,994) which is the U.S. National Phase Under 35 U.S.C. §371 of PCT/US2006/037057 filed Sep. 22, 2006, which in turn claims priority to U.S. Ser. No. 60/720,257 filed Sep. 22, 2005, the disclosures of which are hereby incorporated herein by reference.

BACKGROUND OF THE DISCLOSURE

1. Field of the Disclosure

The present disclosure relates in general to pirfenidone, a small drug molecule whose chemical name is 5-methyl-1-phenyl-2-(1H)-pyridone. Specifically, the present disclosure relates to a capsule formulation of pirfenidone including pharmaceutically acceptable excipients. Further provided are methods of using such capsule formulation in the treatment of fibrotic conditions and other disorders mediated by cytokines.

2. Description of the Related Art

Pirfenidone is a non-peptide synthetic molecule with a molecular weight of 185.23 daltons. Its chemical elements are expressed as $C_{12}H_{11}NO$, and its structure is known. The synthesis of pirfenidone has been worked out. Pirfenidone is manufactured and being evaluated clinically as a broad-spectrum anti-fibrotic drug. Pirfenidone has anti-fibrotic properties via: decreased TNF-α expression, decreased PDGF expression, and decreased collagen expression. Several pirfenidone Investigational New Drug Applications (INDs) are currently on file with the U.S. Food and Drug Administration. Phase II human investigations are ongoing or have recently been completed for pulmonary fibrosis, renal glomerulosclerosis, and liver cirrhosis. There have been other Phase II studies that used pirfenidone to treat benign prostate hypertrophy, hypertrophic scarring (keloids), and rheumatoid arthritis.

One important use of pirfenidone is known to be providing therapeutic benefits to patients suffering from fibrosis conditions such as Hermansky-Pudlak Syndrome (HPS) associated pulmonary fibrosis and idiopathic pulmonary fibrosis (IPF). Pirfenidone demonstrates a pharmacologic ability to prevent or remove excessive scar tissue found in fibrosis associated with injured tissues including that of lungs, skin, joints, kidneys, prostate glands, and livers. Published and unpublished basic and clinical research suggests that pirfenidone may safely slow or inhibit the progressive enlargement of fibrotic lesions, remove pre-existing fibrotic lesions, and prevent formation of new fibrotic lesions following tissue injuries.

It is understood that one mechanism by which pirfenidone exerts its therapeutic effects is modulating cytokine actions. Pirfenidone is a potent inhibitor of fibrogenic cytokines and TNF-α. It is well documented that pirfenidone inhibits excessive biosynthesis or release of various fibrogenic cytokines such as TGF-β1, bFGF, PDGF, and EGF. Zhang S et al., Australian and New England Journal Ophthalmology, 26; S74-S76, 1998. Experimental reports also show that pirfenidone blocks the synthesis and release of excessive amounts of TNF-α from macrophages and other cells. Cain et al., International Journal Immunopharmacology, 20:685-695 (1998).

As an investigational drug, pirfenidone is provided in tablet and capsule forms principally for oral administration. Various formulations have been tested and adopted in clinical trials and other research and experiments. The effectiveness of a formulation may be determined by a plurality of factors, including the amount of pirfenidone it contains, the kinds and relative amounts of pharmacologically acceptable excipients used, and the target patient profile (e.g., the physiological and genetic conditions, disease prognosis, and demographic characteristics of the patient). Changes in these factors cause changes in pharmacokinetic (PK) responses in the patient. Thus, there is a need in general for effective pharmaceutical formulations that elicit desirable pharmacokinetic responses in patients thereby optimizing therapeutic actions of pirfenidone.

SUMMARY OF THE VARIOUS EMBODIMENTS

It is therefore an object of this disclosure to provide pharmaceutical formulations of pirfenidone capable of advantageous therapeutic actions. It is a related object to provide pharmaceutical formulations of pirfenidone capable of eliciting and sustaining desirable pharmacokinetic responses in the patient in need thereof. It is another object of this disclosure to provide methods for treating fibrotic conditions and other cytokine-mediated disorders using such formulations.

In accordance with this disclosure, there is provided, in one embodiment, a capsule having a pharmaceutical formulation of 5-methyl-1-phenyl-2-(1H)-pyridone (pirfenidone), which includes 5-30% of pharmaceutically acceptable excipients and 70-95% of pirfenidone by weight.

According to another embodiment, the excipients include disintegrators, binders, fillers, and lubricants. Examples of disintegrators include agar-agar, algins, calcium carbonate, carboxmethylcellulose, cellulose, clays, colloid silicon dioxide, croscarmellose sodium, crospovidone, gums, magnesium aluminium silicate, methylcellulose, polacrilin potassium, sodium alginate, low substituted hydroxypropylcellulose, and cross-linked polyvinylpyrrolidone hydroxypropylcellulose, sodium starch glycolate, and starch. Examples of binders include microcrystalline cellulose, hydroxymethyl cellulose, hydroxypropylcellulose, and polyvinylpyrrolidone. Examples of fillers include calcium carbonate, calcium phosphate, dibasic calcium phosphate, tribasic calcium sulfate, calcium carboxymethylcellulose, cellulose, dextrin derivatives, dextrin, dextrose, fructose, lactitol, lactose, magnesium carbonate, magnesium oxide, maltitol, maltodextrins, maltose, sorbitol, starch, sucrose, sugar, and xylitol. Examples of lubricants include agar, calcium stearate, ethyl oleate, ethyl laureate, glycerin, glyceryl palmitostearate, hydrogenated vegetable oil, magnesium oxide, magnesium stearate, mannitol, poloxamer, glycols, sodium benzoate, sodium lauryl sulfate, sodium stearyl, sorbitol, stearic acid, talc, and zinc stearate.

According to yet another embodiment, by weight 2-10% of the capsule is disintegrator, 2-30% is binder, 2-30% is filler, and 0.3-0.8% is lubricant. In another embodiment, by weight 2-10% of the capsule is disintegrator, 2-25% is binder, 2-25% is filler, and 0.3-0.8% is lubricant. According to still another embodiment, the excipients further include povidone. In a further embodiment, by weight 1-4% of the capsule is povidone. According to another embodiment, the capsule includes 100-400 mg Pirfenidone.

In accordance with this disclosure, there is provided, in another embodiment, a method for treating a fibrotic condition. The method comprises administering the aforementioned capsule to a patient suffering from the fibrotic condition. Examples of such fibrotic conditions include pulmonary fibrosis, hepatic fibrosis, cardiac fibrosis, keloid, dermal fibrosis, coronary restenosis, and post-surgical adhesions. Examples of pulmonary fibrosis include idiopathic pulmonary fibrosis and Hermansky-Pudlak Syndromes.

In accordance with this disclosure, there is provided, in yet another embodiment, a method for inhibiting actions of cytokines in a patient suffering from a disorder mediated by such cytokines. The method comprises administering the aforementioned capsule to the patient. Examples of such cytokines include TNF-α, TGF-β1, bFGF, PDGF, and EGF. Examples of such disorder include multiple sclerosis, arthritis, asthma, chronic rhinitis, and edema. In still another embodiment, the method further comprises administering one or more capsules to the patient one or more times a day, with a total daily intake of pirfenidone greater than 1200 mg. In various embodiments, the patient is given one or more capsules twice or three times a day.

In accordance with this disclosure, there is provided, in still another embodiment, a capsule having an effective amount of pirfenidone and pharmaceutically acceptable excipients. The capsule when administered in a patient is capable of sustaining a measurable pharmacokinetic response. The pharmacokinetic response is characterized by an increase in the $T_{max}$ or AUC values than a pirfenidone capsule containing no pharmaceutically acceptable excipients. In various embodiments, treatment methods of administering such capsules are provided for patients suffering from fibrotic conditions such as idiopathic pulmonary fibrosis and Hermansky-Pudlak Syndrome, and other disorders mediated by cytokines such as TNF-α, TGF-β1, bFGF, PDGF, and EGF.

BRIEF DESCRIPTION OF THE DRAWINGS

FIG. 2 is a table that shows quantitative compositions of the pirfenidone tablets used in Shionogi Phase II.

FIG. 5 is a table that shows the PK values of the capsules with excipients according to one embodiment of this disclosure, compared to the PK values of capsules without excipients of one of the previously reported PK studies.

FIG. 6 is a table that shows the formulation of pirfenidone/excipient-containing capsules used in the study depicted in FIG. 4 and the study depicted in FIG. 8a-c.

FIG. 7 is a table that lists the components used to prepare a representative batch of the pirfenidone/excipient formulation of FIG. 6.

FIGS. 8a-c lists tables that show the stability of the pirfenidone/excipient formulation of FIG. 6 at 25° C. and 60% relative humidity (FIG. 8a), 35° C. and 65% relative humidity (FIG. 8b), and 40° C. and 75% relative humidity (FIG. 8c).

FIGS. 9a and 9b depict additional representative formulation of pirfenidone/excipient-containing capsules contemplated herein.

DETAILED DESCRIPTION OF THE VARIOUS EMBODIMENTS

Discussion of the Relevant Terms

Figure 1:
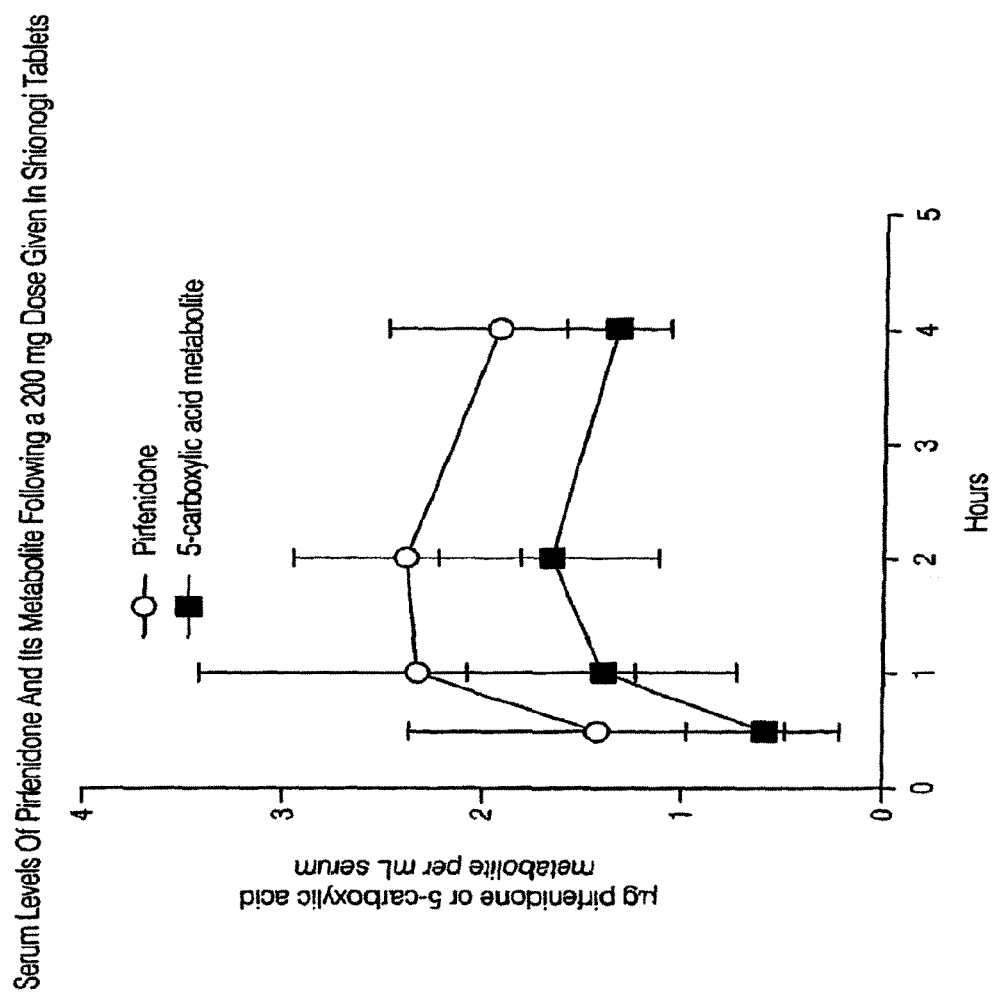
FIG. 1 shows changes in the mean serum concentrations of pirfenidone and its metabolite 5-carboxylic acid over time in human subjects included in one of the previously reported pharmacokinetic studies: Shionogi Phase II.

Throughout the present disclosure relevant terms are to be understood consistently with their typical meanings established in the relevant art, i.e. the art of pharmaceutical chemistry, medicine, biology, genetics, molecular biology, biochemistry, physiology, genomics, pharmacogenomics, bioinformatics, computational biology, and cheminfomatics. However, further clarifications and descriptions are provided for certain terms as set forth below:

The terms pharmaceuticals, pharmaceutical products, drug products, drug chemicals, drug compounds, compounds, and chemicals, are used interchangeably throughout this disclosure.

API, as used herein, refers to active pharmaceutical ingredients. In various embodiments of this disclosure, the API of the capsule and tablet formulations is pirfenidone.

The terms pharmaceutically acceptable excipients, pharmaceutically compatible excipients, and excipients are used interchangeably in this disclosure. They refer to non-API substances such as disintegrators, binders, fillers, and lubricants used in formulating pharmaceutical products. They are generally safe for administering to humans according to established governmental standards, including those promulgated by the United States Food and Drug Administration.

Disintegrators, as used herein, refer to one or more of agar-agar, algins, calcium carbonate, carboxymethylcellulose, cellulose, clays, colloid silicon dioxide, croscarmellose sodium, crospovidone, gums, magnesium aluminium silicate, methylcellulose, polacrilin potassium, sodium alginate, low substituted hydroxypropylcellulose, and cross-linked polyvinylpyrrolidone hydroxypropylcellulose, sodium starch glycolate, and starch.

Binders, as used herein, refer to one or more of microcrystalline cellulose, hydroxymethyl cellulose, hydroxypropylcellulose, and polyvinylpyrrolidone.

Fillers, as used herein, refer to one or more of calcium carbonate, calcium phosphate, dibasic calcium phosphate, tribasic calcium sulfate, calcium carboxymethylcellulose, cellulose, dextrin derivatives, dextrin, dextrose, fructose, lactitol, lactose, magnesium carbonate, magnesium oxide, maltitol, maltodextrins, maltose, sorbitol, starch, sucrose, sugar, and xylitol.

Lubricants, as used herein, refer to one or more of agar, calcium stearate, ethyl oleate, ethyl laureate, glycerin, glyceryl palmitostearate, hydrogenated vegetable oil, magnesium oxide, magnesium stearate, mannitol, poloxamer, glycols, sodium benzoate, sodium lauryl sulfate, sodium stearyl, sorbitol, stearic acid, talc, and zinc stearate.

Capsule, as used herein, refers to a generally safe, readily dissolvable enclosure for carrying certain pharmaceutical products. In one embodiment, capsule is made of gelatin. Other suitable matrix substances such as total synthetic polymer chemicals having gelatin-like properties may be used to manufacture pirfenidone capsules according to alternative embodiments of this disclosure.

AUC, as used herein, refers to the area under the curve that represents changes in blood concentrations of pirfenidone over time.

$C_{max}$, as used herein, refers to the maximum value of blood concentration shown on the curve that represents changes in blood concentrations of pirfenidone over time.

$T_{max}$, as used herein, refers to the time that it takes for pirfenidone blood concentration to reach the maximum value.

$T_{1/2}$, as used in this disclosure, refers to the time that it takes for pirfenidone blood concentration to decline to one-half of the maximum level.

Collectively AUC, $C_{max}$, $T_{max}$, and $T_{1/2}$ are the principle pharmacokinetic parameters that characterize the pharmacokinetic responses of a particular drug product such as pirfenidone in an animal or human subject.

Reported Pharmacokinetic Studies on Pirfenidone

Several pharmacokinetic studies on human subjects have been reported, including one in healthy adult males (Schmidt R M, Ritter A and Margolin S, 1974 Bioavailability of Pirfenidone Capsules Following Oral Administration (Human Volunteers) (60-244-73), Oct. 11, 1974. Affiliated Medical Research, Inc., Princeton, N.J., hereafter "Schmidt 1974"), and two in patients with pulmonary fibrosis (Nagai S, Hamada K, Shigematsu M, Taniyama M, Yamauchi S and Izumi T, 2002, Open Label Compassionate Use One Year-Treatment with Pirfenidone to Patients with Chronic Pulmonary Fibrosis, Intern Med 41: 1118-1123, hereafter "Nagai 2002"; and Azuma A, Nukiwa T, Tsuboi E et al, 2005, Double-Blind, Placebo Controlled Trial of Pirfenidone in Patients with Idiopathic Pulmonary Fibrosis, Am J Respir Crit Care Med., hereafter "Shionogi Phase II").

One additional pharmacokinetic study was conducted on a single dose of four 100 mg capsules each containing 100% pirfenidone. Pirfenidone was administered orally to 10 healthy adult males at doses of 100, 200, and 400 mg. On day 1, a single dose of 100 mg was given to each subject. On day 3, a single dose of 200 mg was given to each subject. And on day 4, a last single dose of 400 mg was given to each subject. This last single dose of 400 mg was analyzed for pharmacokinetics. Blood plasma samples were collected before dosing and at 0.25, 1, 4, and 6 hr after dosing. Pirfenidone concentrations in plasma were determined by gas chromatography. The resulting values of pharmacokinetic parameters are: $C_{max}$=6.3+2.5 µg/mL, $T_{max}$=0.9±0.3 hrs, $AUC_{6hr}$=20.8±10.0 µg/mL-hr, and $T_{1/2}$=2.2±0.6 hrs.

Nagai 2002 involved 10 male patients with pulmonary fibrosis. The subjects underwent dose escalation starting with an initial dose of 400 mg for several days to a maintenance dose of 40 mg/kg/day. Pharmacokinetics analyses were done on each of the 10 subjects on day 1 when a dose of 400 mg was given. Plasma samples were collected at 0, 0.25, 1, 1.5, 2, 4, 6, 8, and 24 hr after dosing. The values of pharmacokinetic parameters were computed. $C_{max}$ was 3.0 to 7.2 µg/mL, and $AUC_{24hr}$ was 16.9 to 66.4 µg/mL·hr.

Shionogi Phase II involved serial sampling in a 15-patient subset of a pirfenidone cohort (13 males and 2 females). On day 1 a 200 mg single dose was given to each of the 15 patients, and serum samples were collected before dosing and at 0.5, 1, 2, and 3 hr after dosing. Blood concentrations of pirfenidone were determined by HPLC assay. FIG. 1 demonstrates changes in the observed mean serum concentrations of pirfenidone and its metabolite 5-carboxylic acid over time. The values of pharmacokinetic parameters were computed to be: $C_{max}$=2.7±0.7 µg/mL, $T_{max}$=1.8±1.1 hrs, $AUC_{4hr}$=7.3±1.6 µg/mL·hr, and $T_{1/2}$=3.5±2.2 hrs.

The drug formulations in these previously reported studies were different. Schmidt 1974 used a capsule including 100% pirfenidone. Nagai 2002 and Shionogi Phase II used pirfenidone tablets that included certain pharmaceutically acceptable excipients. For example, the drug product used in Shionogi Phase II was formulated as compressed, coated tablets of 200 mg of pirfenidone. Shionogi Phase II tablets included pharmaceutically acceptable excipients. FIG. 2 is a table listing the ingredients of the Shionogi Phase II tablets and the quantities of each ingredient. As shown, the core tablet was 285 mg, of which 200 mg was API. Various amounts of disintegrator, filler, binder, and lubricant were included. With the addition of the coating, the total weight of the Shionogi Phase II tablet was 296.4 mg.

Figure 3:
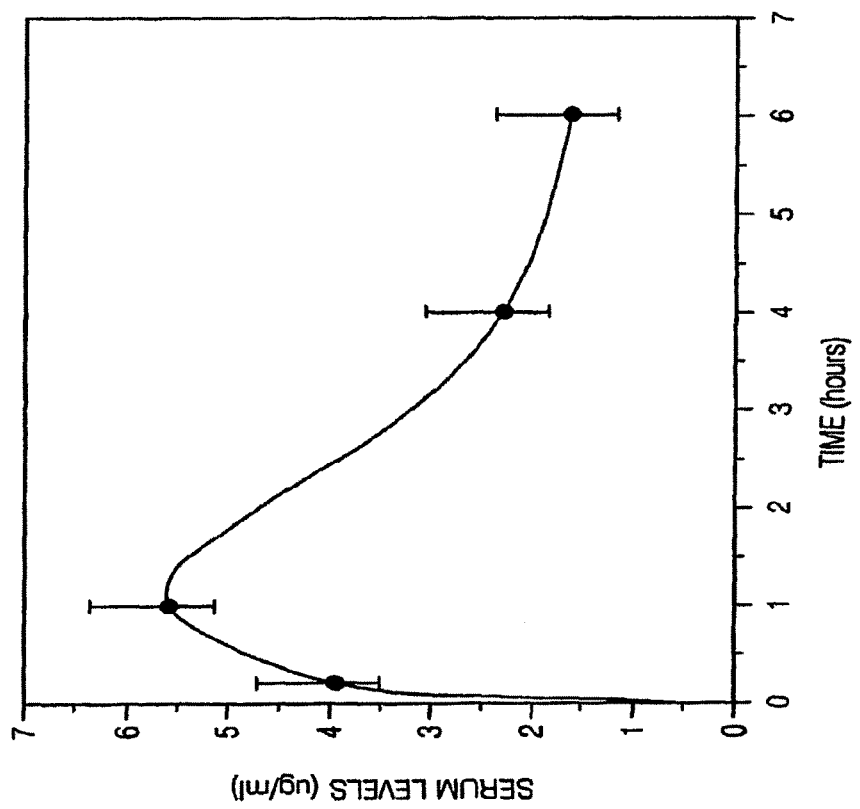
FIG. 3 shows changes in pirfenidone serum concentrations over time in human subjects after a single dose of 400 mg pirfenidone delivered orally in capsules without excipients.

Schmidt 1974 examined the pharmacokinetics of single dose pirfenidone. Ten human volunteers were included in this study. At 15 minutes after oral ingestion of 400 mg pirfenidone, the average serum concentration of pirfenidone reached 3.97 mg/mL. At one hour, the average serum concentration was measured to be 5.57 mg/mL, and at six hour 1.63 mg/mL. FIG. 3 is a plot of serum pirfenidone levels over time summarizing this study. As shown, the maximum serum pirfenidone level was reached between one and three hours. The value of $T_{1/2}$ was calculated to be 2.87+0.22 hrs.

Capsule Formulation of Pirfenidone with Excipients

To those skilled in the pharmaceutical research and manufacturing, it is generally known that tablet formulations permit generous additions of non-API ingredients including excipients and coating substances, especially high percentage of fillers. However, the addition of non-API ingredients may limit the amount of API carried in each tablet. By contrast, capsule formulations tend to facilitate the inclusion of high percentage of API with no or less non-API components. Capsules may allow for inclusion of a larger amount of binders, instead of fillers as used more in tablets. Where high percentage of API is desired and specific excipients are not known to be essential, capsule formulations are often adopted.

To be sure, no capsule formulation of pirfenidone manufactured or reported to date contains excipients. The present disclosure provides a new pirfenidone capsule formulation with certain pharmaceutically acceptable excipients. According to one embodiment, this new capsule formulation is capable of eliciting advantageous pharmacokinetic responses in human subjects. In another embodiment, this new capsule formulation facilitates dissolution and improves flowability in the capsule manufacturing process.

This capsule formulation includes 100-400 mg pirfenidone. One or more pharmaceutically acceptable excipients are added in various embodiments. For example, in one embodiment, by weight 2-10% of the capsule is disintegrator, 2-30% is binder, 2-30% is filler, and 0.3-0.8% is lubricant. As described in the beginning of this Detailed Description, a multitude of substances may be suitably included as disintegrator, binder, filler, and lubricant. One example is to use magnesium stearate as lubricant, microcrystalline cellulose as binder, and croscarmellose as disintegrator. In a particular embodiment, the capsule formulation further includes povidone. By weight povidone may constitute 1-4% of the capsule.

The capsule shell may be made of hard gelatin in one embodiment. The shell may be clear or opaque, white or with color in various embodiments. The capsule is size 1 in a preferred embodiment. Other sizes may be adopted in alternative embodiments.

The manufacture of pirfenidone capsules based on the capsule formulation of the various embodiments includes a series of steps. These steps are: preparing pirfenidone granulation, fluid bed drying, milling, lubrication blend, encapsulation, and bulk packaging The preparation of pirfenidone granulation may be done in the following sequence. First, povidone is mixed with water and dissolved using an overhead mixer. Second, pirfenidone is milled with croscarmellose and microcrystalline cellulose to break up any lumps. Third, the milled pirfenidone, croscarmellose, and microcrystalline cellulose are added into a high sheer granulator and blended. Fourth, the povidone and water solution is added to the blend. Fifth, the pirfenidone granulation is blended for an additional period of time after the povidone and water solution have been completely added.

The fluid bed drying process may be performed on a Fluid Bed Dryer with an inlet temperature of 60° C. The milling process may be performed using a suitable miller such as Quadro Comil®. The lubrication blend process may be conducted with the addition of an appropriate amount of croscarmellose and magnesium stearate. The pirfenidone granulation may be further blended at this point. Next the pirfenidone granulation is encapsulated using a suitable encapsulator into two-piece, size 1, gelatin capsules to yield a desired pirfenidone dose of 100-400 mg. The dose of 200-300 mg is yielded in a preferred embodiment. To conclude the capsule manufacturing process, finished capsules may be packaged in secured, double polybags and stored at controlled room temperature. Those skilled in drug research and drug making will appreciate that certain of the aforementioned steps may be modified or omitted, and additional steps may be included, without materially altering the outcome of the manufacturing.

An exemplary composition of the pirfenidone/excipient formulation-containing capsules that was prepared and tested is provided in FIG. 6. A representative batch of the pirfenidone/excipient formulation was prepared using routine wet formulation methods to combine the components listed in FIG. 7.

Figure 4:
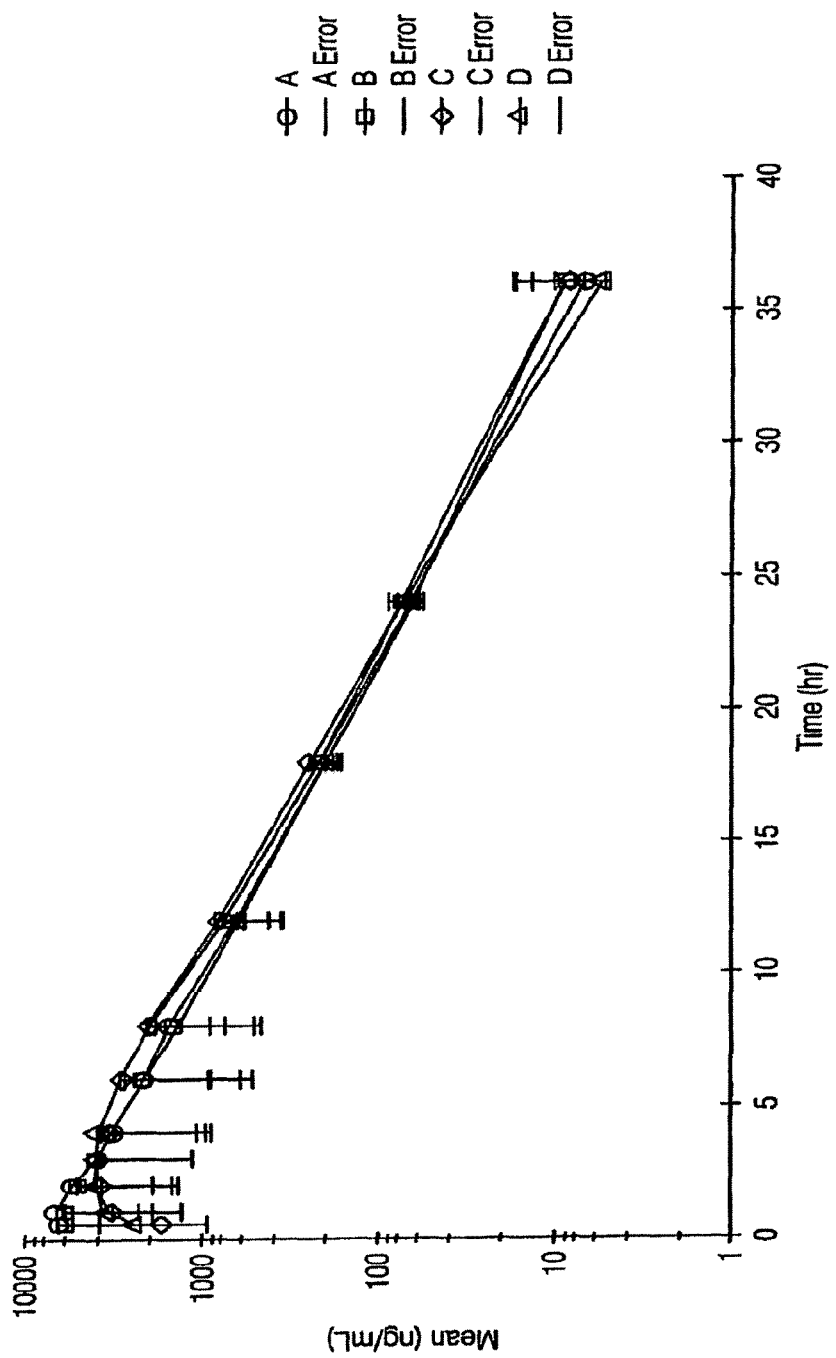
FIG. 4 shows changes in pirfenidone serum concentrations over time in human objects following a single dose of 200-300 mg pirfenidone delivered orally in capsules with excipients, according to one embodiment of this disclosure.

Pharmacokinetic studies were performed on the pirfenidone capsules of the present disclosure. A first study depicted in FIG. 4 shows average changes in serum concentrations over time in four groups of subjects to whom were administered a single dose of the 267 mg pirfenidone capsule formulation of FIG. 6. The four lines of this graph, A, B, C, and D, represent four different groups of subjects: A, fasted subjects; B, fasted subjected with antacid administered; C, fed subjects; and D, fed subjects with antacid administered.

In another pharmacokinetic study, two groups of human subjects on normal diet were included, each having 13 subjects. One group (Group I) received no antacid, while the other group (Group II) received antacid. The 267 mg pirfenidone capsule formulation of FIG. 6 was given to each subject. FIG. 5 is a table summarizing the resulting PK values for both groups (Capsule Groups I and II), compared to the PK values reported in the one additional pharmacokinetic study of a capsule of pirfenidone only. As demonstrated in FIG. 5, $T_{max}$ is significantly longer (an approximately two-fold increase in each of Groups I and II) for these excipient-containing capsules than what was reported in the one additional pharmacokinetic study of a capsule of pirfenidone only. AUC is also significantly higher for these excipient-containing capsules than what was reported in the one additional pharmacokinetic study of a capsule of pirfenidone only. AUC values are computed over a time period of zero to infinity. The values of $C_{max}$ and $T_{1/2}$ are also higher than or comparable with those reported in the one additional pharmacokinetic study of a capsule of pirfenidone only.

These resulting PK values, especially the increased $T_{max}$ and AUC, indicate a prolonged absorption phase for the pirfenidone capsules with excipients according to the present disclosure. Consequently, these capsules are capable of sustaining prolonged therapeutic actions in a patient. Therefore, compared to the capsules without excipients, as what were used in Schmidt 1974, the capsule formulation with the excipients may be advantageously administered to a patient in need, thereby eliciting desirable pharmacokinetic responses in the patient. Whilst such desirable PK responses are surprising results, it is conceivable that binders such as microcrystalline cellulose or povidone favorably interact with the amide carbonyl group of pirfenidone forming a transient complex which may then dissociate, resulting in a slow build-up in the plasma concentration of pirfenidone, or a slow decline or clearance in the plasma concentration.

In addition to the therapeutic advantages of the pirfenidone/excipient formulations provided herein, these capsules and the formulations also show good stability under various storage conditions over time. In some embodiments, under various storage conditions the capsules and pirfenidone/excipient formulations provided herein can be stable for at least, or at least about, 3 months, 6 months, 9 months, 12 months, 15 months, 18 months, 24 months, 36 months, or 48 months. For example, under storage conditions of 25° C. and 60% relative humidity, the capsules and pirfenidone/excipient formulations provided herein can be stable for at least, or at least about, 3 months, 6 months, 9 months, 12 months, 15 months, 18 months, 24 months, 36 months, or 48 months. In another example, under storage conditions of 30° C. and 65% relative humidity, the capsules and pirfenidone/excipient formulations provided herein can be stable for at least, or at least about, 3 months, 6 months, 9 months, 12 months, 15 months, 18 months, 24 months, 36 months, or 48 months. In another example, under storage conditions of 40° C. and 75% relative humidity, the capsules and pirfenidone/excipient formulations provided herein can be stable for at least, or at least about, 3 months, 6 months, 9 months, or 12 months.

In some embodiments, the stability of the capsules and pirfenidone/excipient formulations provided herein is determined by measuring the dissolution rate of the stored capsule and/or pirfenidone/excipient formulations. Any of a variety of dissolution methods provided herein or otherwise known in the art can be performed to determine the stability of capsules and pirfenidone/excipient formulations. Dissolution measurements are in vitro methods known in the art to be representative of in vivo $T_{max}$ and AUC values. Accordingly, the stability of the capsules and pirfenidone/excipient formulations as measured by dissolution methods will be representative of the in vivo $T_{max}$ and AUC values of a subject when the capsules and pirfenidone/excipient formulations after storage, for example, under the above-exemplified conditions for the indicated amount of time. Typically, a dissolution level indicative of an acceptable level of stability is a dissolution of at least, or at least about 80%, 85%, 90%, 91%, 92%, 93%, 94%, 95%, 96%, 97%, 98%, 99%, or more, of the pirfenidone in the capsules provided herein. Any of a variety of dissolution methods provided herein or otherwise known in the art can be performed to determine the stability of capsules and pirfenidone/excipient formulations. For example, dissolution can be determined according to the pharmacopoeial dissolution method specified in USP29.

The stability of the capsules and pirfenidone/excipient formulations provided herein is demonstrated in the results presented in FIG. 8. The 267 mg pirfenidone capsule formulation of FIG. 6 was stored for 18 months under three different storage conditions: 25° C. and 60% relative humidity, 30° C. and 65% relative humidity, and 40° C. and 75% relative humidity. FIG. 8 shows that the dissolution of the capsule and pirfenidone/excipient formuations at 25° C. and 60% relative humidity, 30° C. and 65% relative humidity did not appreciably change over the duration of the 18 month period. The dissolution of the capsule and pirfenidone/excipient formuations at 40° C. and 75% relative humidity did not appreciably change over the initial 12 month period. The dissolution analysis was performed according to the pharmacopoeial dissolution method specified in USP29 using Apparatus 2 (paddles) with water as a solvent and a specification of Q≥70% of label claim in 30 minutes. Also shown in FIG. 8, the level of impurities in each formulation, as determined by HPLC, was less than 0.05% over the duration of the 18 month period. In addition, the moisture content, as determined by the Karl Fischer method, of all but one time point (40° C., 75% RH at 18 months) remained below 2%, and the moisture content of all samples remained below 2.5% over the duration of the 18 month period. Finally, the percent of pirfenidone in each sample, as determined by HPLC, showed no appreciable degradation over the 18 month period.

In addition to the specific formulation provided herein in FIG. 6, further formulations contemplated herein are provided in FIGS. 9a and 9b.

Therapeutic Indications

One embodiment of this disclosure provides methods for treating fibrotic conditions and other cytokine-mediated disorders. These methods comprise administering the excipients-containing pirfenidone capsules of this disclosure to a patient suffering from a fibrotic condition or a cytokine-mediated disorder. The dosing may be twice or three times daily, with one or more capsules per intake. According to a particularly embodiment, the total daily intake is at least 1200 mg pirfenidone. The total daily intake amount may vary, depending on the patient profile, including among other things the patient's demographic characteristics, physiological and genetic conditions, and disease prognosis. For example, a child or a senior person may be given a lower amount daily than that given to an ordinary adult.

The anti-fibrotic activity of pirfenidone is demonstrated in vivo animal fibrosis models, as well as in vitro cell culture studies with human or animal lung fibroblasts, dermal fibroblasts, and fibroblast-like cells. Those data indicates that pirfenidone may be an effective agent for preventing and treating post-surgical adhesions, myocardial fibrosis, renal fibrosis, liver cirrhosis, atherosclerosis, and other fibrotic disorders. In vitro cell cultures with human mesenchymal-like cells (including lung fibroblasts, skin fibroblasts, prostate stromal cells, and renal mesangial cells, etc) have shown pharmacologic inhibition by pirfenidone of excessive cell proliferation induced by cytokine growth factors (TGF-β1, bFGF, PDGF, and EGF). In cell culture media, graded concentrations of pirfenidone were effective at levels which were ten to twenty times lower than those exerting any pharmacologically toxic effects on the cells.

At the site of injury, otherwise normal resident cells (e.g., fibroblasts, pericytes, mesangial cells, astrocytes, microglia, and oligodendrocytes) manufacture and discharge high concentrations of growth factors into adjacent tissue spaces. These resident sources of pathologically high levels of growth factors are directly responsible for the persistently excessive levels of growth factors. They cause excessive and harmful formation of collagen or amyloid matrix as well as damage to adjacent cells, the associated organ dysfunction, and frequently, organ malformation.

TGF-β1 is a potent growth-related peptide whose effects may be observed at femtomolar concentrations. It appears to be ubiquitous, and is a bifunctional regulator of cell proliferation in vitro. It acts either as a mitogen or a growth inhibitor depending on tissue concentration and the state of cell confluence (L. J. Striker et al., Lab. Invest. 64:446-456, 1991). In skin incisions, after attracting macrophages and fibroblasts, TGF-β1 enhances extracellular matrix formation by increasing transcription of genes for collagen and fibronectin, decreasing secretion of proteases, increasing secretion of protease inhibitors, and increasing transcription of cellular receptors for matrix proteins.

The anti-fibrotic activities of pirfenidone have been demonstrated in vivo in laboratory animals with fibrotic lesions, in vitro with human lung fibroblast (WI38) cell cultures, and observed through pilot open trials in patients with severe pulmonary fibrosis, benign prostate hypertrophy, or keloids. Pirfenidone may selectively arrest scar enlargement, and remodels or removes scar tissue or fibrosis. The dysfunction caused by fibrotic lesions may be ameliorated by the reduction or removal of the fibrotic lesion following pirfenidone treatment. Apparently organ and tissue function can be restored, even after the presence of fibrosis for several years. When given immediately after an insult, such as trauma, infection, or allergy, to a tissue, pirfenidone also may prevent formation of excessive scar tissue, or fibrotic lesions, and thus help retain normal function and appearance of the tissue.

Pirfenidone may cause removal of excessive collagenous fibrotic tissue by a phagocytic action of local fibroblasts. This has been observed by examination of histological sections of lung tissue under the light microscope from dogs, mice, rats, and hamsters with pulmonary fibrosis treated with pirfenidone, and also through the electron micrographs of histological sections of lung tissue taken from hamsters with experimentally-induced asbestosis that were treated with pirfenidone. No infiltration of inflammation-inducing neutrophils, PMN cells, monocytes, lymphocytes occurred.

The enhanced proliferation of WI38 fibroblasts upon in vitro exposure to PDGF or bFGF may be blocked by pirfenidone added to cell growth media. Pirfenidone may also inhibit the TGF-β1 induced rise in collagen output in lung and dermal fibroblast cultures.

The human clinical findings after treatment with pirfenidone have been consistent with the anti-fibrotic effects observed in the laboratory animals. Pilot open clinical trials with oral pirfenidone have been undertaken with patients afflicted with pulmonary asbestosis, bleomycin-induced pulmonary fibrosis, idiopathic pulmonary fibrosis, scleroderma with pulmonary fibrosis, and Hermansky-Pudlak Syndrome characterized by pulmonary fibrosis.

The clinical criteria for beneficial response during the first months on pirfenidone included reduction in incidence of coughs, reduction in supplemental oxygen requirements, increased exercise tolerance, reduced dyspnea during exercise, amelioration of cor pulmonale, resumption of normal daily tasks, body weight gain, and survival. During the early months, pulmonary function as gauged by chest x-ray, spirometry, or CO diffusion (DLCO) showed little, if any, change. However, after 4 to 6 months on pirfenidone, inhibition or blocking of further deterioration in lung function was evidenced by pulmonary function tests, vital capacity (VC), in the diffusing capacity of the lung for carbon monoxide (DLCO). These overall observations compare favorably with those described by Van Barneveld et al. (Amer. Rev. Respr. Dis., vol. 135, 48-51, 1987), during the spontaneous recovery by patients from bleomycin-induced pulmonary pneumonitis (early stage fibrosis).

Martinet et al. (NE Jour. Med., vol 317, 202-209, 1987) have described an exaggerated release of PDGF by alveolar macrophages in patients with idiopathic pulmonary fibrosis. The in vitro demonstration of inhibition by pirfenidone of the mitogenesis and enhanced formation of collagen caused by growth factors (bFGF, PDGF, and TGF-β1) may partly explain the beneficial in vivo anti-fibrotic action of pirfenidone.

In an open pilot trial of pirfenidone in older men with clinically advanced benign prostate hypertrophy (BPH, non-cancerous fibrous enlargement of the male prostate gland), the patients experienced functional improvement based on objective criteria. After taking oral pirfenidone the frequent urinary bladder urgency was ameliorated, and nocturia rarely recurred. In another pilot open trial, topical applications of pirfenidone ointment to surgical sites immediately after keloid resection has prevented recurrence of the keloids as observed in two-year follow-ups in the patients. Each of those patients had a prior history of repeated early keloid re-growths after such surgery. Pirfenidone may induce a remodeling of skin fibrotic lesions to reduce or remove keloids, reduce or remove dermal scars, and remove or lessen the contractures of hypertrophic (post burn injury) scars. In a similar condition, pirfenidone also acts to inhibit post-operative surgical adhesions.

Thus, clinical investigations under both controlled protocol designs and open label trials have demonstrated that pirfenidone exerts anti-fibrotic and cytoprotective actions. The observed side effects after oral administration were relatively mild (drowsiness, gastric nausea or photosensitivity rash). No serious adverse reactions have been reported.

In summary, based on the TNF-α inhibitor (cytoprotective) activity of pirfenidone, the capsule formulation of the present disclosure may be administered according to certain embodiments of this disclosure to treat patients suffering from the following disorders:

1) Central Nervous System syndromes: relapsing-remitting multiple sclerosis, primary and secondary multiple sclerosis, spinal multiple sclerosis, cerebral malaria, viral or bacterial infections of the CNS, bacterial meningitis, "autoimmune" disorders of the central nervous system (CNS), CNS stroke and infarction, brain edema, Parkinson's syndrome, Alzheimer's disease, amylotrophic lateral sclerosis (ALS), and brain concussion or contusion;

2) Musculo-skeletal syndromes: rheumatoid arthritis, trauma-induced arthritis, arthritis caused by a microbial infection, or by a parasite, tendonitis, and, arthritis induced by medical products or drugs (including small synthetic molecules as well as purified natural or synthesized peptides or proteins);

3) Pulmonary syndromes: acute adult respiratory distress syndrome, asthma, allergic rhinitis, allergic conjunctivitis, chronic obstructive pulmonary disease (COPD), and lung sarcoidosis;

4) Systemic immunologic, inflammatory or toxic syndromes: endotoxemia shock syndrome, septic shock, grafthost disease, allograft vasculopathy, hemorrhagic shock, reperfusion injury of the brain or myocardium, thermal burns, radiation injury, general or dermal traumatic or contusion injuries, eosinophilic granuloma, diabetic mellitus (type II), or systemic lupus erythromatosus;

5) Gastro-intestinal syndromes: Crohn's disease, ulcerative colitis, and liver inflammatory disorders; and 6) Congestive heart failure.

Further, based on the anti-fibrotic activity of pirfenidone, the capsule formulation of the present disclosure may be administered according to other embodiments to treat patients suffering from the following disorders: pulmonary fibrosis, radiation and drug-induced lung fibrosis, hepatic fibrosis, cardiac fibrosis, keloid, post-surgical adhesions, benign prostate hypertrophy in humans, arteriosclerosis, dermal fibrosis, and coronary restenosis.

It is to be understood that the description, specific examples and data, while indicating exemplary embodiments, are given by way of illustration and are not intended to limit the various embodiments of the present disclosure. All references cited herein for any reason, are specifically and entirely incorporated by reference. Various changes and modifications within the present disclosure will become apparent to the skilled artisan from the description and data contained herein, and thus are considered part of the various embodiments of this disclosure.

What is claimed is:

1. A capsule comprising a pharmaceutical formulation of 5-methyl-1-phenyl-2-(1H)-pyridone, wherein said pharmaceutical formulation comprises pharmaceutically acceptable excipients and 5-methyl-1-phenyl-2-(1H)-pyridone, and the formulation is stable for at least 9 months at 40° C. at 75% relative humidity, as measured by a dissolution of at least 85% of the 5-methyl-1-phenyl-2-(1H)-pyridone after the at least 9 months.

2. The capsule of claim 1, wherein said excipients comprise one or more selected from the group consisting of disintegrators, binders, fillers, and lubricants.

3. The capsule of claim 2, wherein said disintegrators comprise one or more selected from the group consisting of agar-agar, algins, calcium carbonate, carboxmethylcellulose, cellulose, clays, colloid silicon dioxide, croscarmellose sodium, crospovidone, gums, magnesium aluminium silicate, methylcellulose, polacrilin potassium, sodium alginate, low substituted hydroxypropylcellulose, and cross-linked polyvinylpyrrolidone hydroxypropylcellulose, sodium starch glycolate, and starch.

4. The capsule of claim 2, wherein said binders comprise one or more selected from the group consisting of microcrystalline cellulose, hydroxymethyl cellulose, hydroxypropylcellulose, and polyvinylpyrrolidone.

5. The capsule of claim 2, wherein said fillers comprise one or more selected from the group consisting of calcium carbonate, calcium phosphate, dibasic calcium phosphate, tribasic calcium sulfate, calcium carboxymethylcellulose, cellulose, dextrates, dextrin, dextrose, fructose, lactitol, lactose, magnesium carbonate, magnesium oxide, matitol, maltodextrins, maltose, sorbitol, starch, sucrose, sugar, and xylitol.

6. The capsule of claim 2, wherein said lubricants comprise one or more selected from the group consisting of agar, calcium stearate, ethyl oleate, ethyl laureate, glycerin, glyceryl palmitostearate, hydrogenated vegetable oil, magnesium oxide, magnesium stearate, mannitol, poloxamer, glycols, sodium benzoate, sodium lauryl sulfate, sodium stearyl, sorbitol, stearic acid, talc, and zinc stearate.

7. The capsule of claim 2, wherein by weight said disintegrator is 2-10%, said binder is 2-30%, said filler is 2-30%, and said lubricant is 0.3-0.8%.

8. The capsule of claim 2, wherein said excipients further comprise povidone.

9. The capsule of claim 8, wherein by weight said povidone is 1-4%.

10. The capsule of claim 9, wherein the capsule comprises 100-400 mg 5-methyl-1-phenyl-2-(1H)-pyridone.

11. A method for treating a fibrotic condition or inhibiting actions of cytokines, comprising administering the capsule of claim 1 to a patient suffering from said fibrotic condition or suffering from a disorder mediated by said cytokines.

12. The method of claim 11, wherein said fibrotic condition is one selected from the group consisting of pulmonary fibrosis, hepatic fibrosis, cardiac fibrosis, keloid, dermal fibrosis, coronary restenosis, and post-surgical adhesions.

13. The method of claim 12, wherein said pulmonary fibrosis is one selected from the group consisting of idiopathic pulmonary fibrosis and Hermansky-Pudlak Syndrome.

14. A method of claim 11, wherein said fibrotic condition is scleroderma with pulmonary fibrosis.

15. The method of claim 11, wherein said cytokines comprise one or more selected from the group consisting of TNF-α, TGF-β1, bFGF, PDGF, and EGF.

16. The method of claim 15, wherein said disorder is one selected from the group consisting of multiple sclerosis, arthritis, asthma, chronic rhinitis, and edema.

17. The method of claim 11, further comprising administering one or more said capsules to said patient one or more times a day, wherein the total intake of 5-methyl-1-phenyl-2-(1H)-pyridone is at least 1200 mg a day.

18. The method of claim 17, wherein said one or more capsules are administered to the patient twice a day.

19. The method of claim 18, wherein said one or more capsules are administered to the patient three times a day.

20. The capsule of claim 8, wherein said povidone comprises at least about 1.85% by weight of the formulation.

21. The capsule of claim 8, wherein said povidone comprises at least about 1% by weight of the formulation.

22. The capsule of claim 2, wherein the formulation comprises a wet-granulated mixture comprising 5-methyl-1-phenyl-2-(1H)-pyridone, binder, filler, and disintegrator.

23. The capsule of claim 2, wherein:
    the pharmaceutically acceptable excipients comprise a lubricant, a filler, and a disintegrator;
    the binder comprises microcrystalline cellulose and povidone;
    the povidone is included in an amount of 1-4% by weight of the formulation;
    the total amount of binder is 2-30% by weight of the formulation; and
    the formulation comprises a wet-granulated mixture comprising the 5-methyl-1-phenyl-2-(1H)-pyridone, the binder, the filler, and the disintegrator.

24. The capsule of claim 1, wherein said pharmaceutical formulation comprises, by weight, 5-30% of the pharmaceutically acceptable excipients and 70-95% of the 5-methyl-1-phenyl-2-(1H)-pyridone.

25. The method of claim 11, wherein the fibrotic condition is a pulmonary fibrotic condition.

26. A capsule comprising a pharmaceutical formulation of 5 methyl-1-phenyl-2-(1H)-pyridone, wherein said pharmaceutical formulation comprises pharmaceutically acceptable excipients and 5-methyl-1-phenyl-2-(1H)-pyridone, and the formulation is stable for at least 18 months at 25° C. at 60% relative humidity, as measured by a dissolution of at least 93% of the 5-methyl-1-phenyl-2-(1H)-pyridone after the at least 18 months.

* * * * *